(12) United States Patent
Govari

(10) Patent No.: US 11,278,350 B2
(45) Date of Patent: *Mar. 22, 2022

(54) ESTIMATION OF TISSUE THICKNESS

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 518 days.

This patent is subject to a terminal disclaimer.

(21) Appl. No.: 15/868,297

(22) Filed: Jan. 11, 2018

(65) Prior Publication Data

US 2018/0228402 A1    Aug. 16, 2018

Related U.S. Application Data

(60) Provisional application No. 62/457,266, filed on Feb. 10, 2017.

(51) Int. Cl.
*A61B 18/14*    (2006.01)
*A61B 18/12*    (2006.01)
(Continued)

(52) U.S. Cl.
CPC ...... *A61B 18/1492* (2013.01); *A61B 18/1233* (2013.01); *A61B 2017/00199* (2013.01);
(Continued)

(58) Field of Classification Search
CPC .......... A61B 2018/00738; A61B 2018/00791; A61B 2018/00773; A61B 18/14;
(Continued)

(56) References Cited

U.S. PATENT DOCUMENTS

2002/0173784 A1    11/2002    Sliwa et al.
2004/0147920 A1*    7/2004    Keidar .................. A61B 5/062
                                                         606/34
(Continued)

FOREIGN PATENT DOCUMENTS

EP    2875791 A1    5/2015
WO    9634569 A1    11/1996

OTHER PUBLICATIONS

Hussein, Ahmed et al., "Ablation Index-guided Pulmonary Vein Isolation for Atrial Fibrillation may Improve Clinical Outcomes in Comparison to Contact Force-guided Ablation", Heart Rhythm Congress, Oct. 12, 2016, p. ii14.

(Continued)

*Primary Examiner* — Jaymi E Della
*Assistant Examiner* — Sean W Collins
(74) *Attorney, Agent, or Firm* — Scully, Scott, Murphy & Presser, PC

(57) ABSTRACT

A method, including performing an initial ablation of a tissue using an electrode in a probe distal end to apply a first power to the tissue, and measuring a change of temperature of the distal end while applying the first power. The method also includes estimating a thickness of the tissue in response to the measured change of temperature, and in response to the estimated thickness, computing at least one of a second power required and a time period for ablation, to complete ablation of the tissue. The method further includes performing a subsequent ablation of the tissue using the computed at least one of the second power and the time period for ablation.

20 Claims, 2 Drawing Sheets

(51) Int. Cl.
*A61B 18/00* (2006.01)
*A61B 90/00* (2016.01)
*A61B 17/00* (2006.01)

(52) U.S. Cl.
CPC ............ *A61B 2018/00029* (2013.01); *A61B 2018/0066* (2013.01); *A61B 2018/00351* (2013.01); *A61B 2018/00357* (2013.01); *A61B 2018/00577* (2013.01); *A61B 2018/00642* (2013.01); *A61B 2018/00684* (2013.01); *A61B 2018/00702* (2013.01); *A61B 2018/00744* (2013.01); *A61B 2018/00761* (2013.01); *A61B 2018/00791* (2013.01); *A61B 2018/00797* (2013.01); *A61B 2018/00839* (2013.01); *A61B 2090/065* (2016.02); *A61B 2218/002* (2013.01)

(58) Field of Classification Search
CPC . A61B 18/1492; A61B 5/1076; A61B 8/4263; A61B 8/429; A61B 2017/00243; A61B 2034/104; A61B 2218/002; A61B 2090/065; A61B 2018/00351; A61B 2018/00577; A61B 2018/00702; A61B 2018/00029; A61B 18/1206; A61B 2018/00357; A61B 5/05; A61B 5/01; A61B 8/12
See application file for complete search history.

(56) References Cited

U.S. PATENT DOCUMENTS

| | | | |
|---|---|---|---|
| 2010/0191142 A1* | 7/2010 | Paul | A61B 5/015 600/549 |
| 2011/0022041 A1* | 1/2011 | Ingle | A61B 18/1492 606/33 |
| 2016/0166309 A1 | 6/2016 | Balasubramanian | |
| 2017/0014181 A1 | 1/2017 | Bar-Tal et al. | |

OTHER PUBLICATIONS

Rozen Guy et al., "Prediction of radiofrequency ablation lesion formation using a novel temperature sensing technology incorporated in a force sensing catheter", Heart Rhythm, Elsevier, US, vol. 14, No. 2, Jan. 16, 2017, pp. 248-254.

* cited by examiner

ESTIMATION OF TISSUE THICKNESS

CROSS-REFERENCE TO RELATED APPLICATION

This application claims the benefit of U.S. Provisional Patent Application 62/457,266, filed 10 Feb. 2017, which is incorporated herein by reference.

FIELD OF THE INVENTION

This invention relates generally to tissue ablation, and specifically to measuring parameters for the ablation.

BACKGROUND OF THE INVENTION

As the heart beats, an electropotential wave travels through the heart approximately once every second, and when the heart acts normally the heart is said to be in sinus rhythm. In abnormal cases, such as when atrial fibrillation occurs, the heart is no longer in sinus rhythm. The fibrillation is caused by incorrect movement of the electropotential wave through the heart.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

performing an initial ablation of a tissue using an electrode in a probe distal end to apply a first power to the tissue;

measuring a change of temperature of the distal end while applying the first power;

estimating a thickness of the tissue in response to the measured change of temperature;

in response to the estimated thickness, computing at least one of a second power required and a time period for ablation, to complete ablation of the tissue; and performing a subsequent ablation of the tissue using the computed at least one of the second power and the time period for ablation.

In a disclosed embodiment the method includes determining a relationship between the change of temperature of the distal end and the thickness of the tissue, and using the relationship in estimating the thickness of the tissue. Typically, the method also includes determining the relationship prior to performing the initial ablation. Alternatively or additionally, the method further includes determining the relationship in response to an injected power applied to the tissue and an irrigation rate for irrigating the tissue.

In a further disclosed embodiment the method includes selecting the first power so that the initial ablation ablates the tissue to a predetermined estimated lesion depth. Typically the method includes computing the at least one of the second power required and the time period in response to a difference between the estimated thickness of the tissue and the predetermined estimated lesion depth.

In a yet further disclosed embodiment the method includes using an ablation index to determine at least one of the first power and the second power.

There is also provided, according to a further embodiment of the present invention, a method, including:

performing an ablation of a tissue using an electrode in a probe distal end to apply a power to the tissue;

measuring a change of temperature of the distal end while applying the power; and estimating a thickness of the tissue in response to the measured change of temperature.

In an alternative embodiment the method includes displaying a value of the estimated thickness of the tissue to an operator performing the ablation.

There is also provided, according to a yet further embodiment of the present invention, apparatus, including:

a probe having a distal end;

an electrode located on the distal end and in contact with tissue;

at least one temperature sensor in the distal end; and a processor, configured to:

perform an initial ablation of the tissue by applying a first power to the tissue with the electrode, measure a change of temperature of the distal end using the at least one temperature sensor while applying the first power, estimate a thickness of the tissue in response to the measured change of temperature, in response to the estimated thickness, compute at least one of a second power required and a time period for ablation, to complete ablation of the tissue, and perform a subsequent ablation of the tissue using the computed at least one of the second power and the time period for ablation.

There is also provided, according to another embodiment of the present invention, apparatus, including:

a probe having a distal end;

an electrode located on the distal end and in contact with tissue;

at least one temperature sensor in the distal end; and a processor, configured to:

perform an initial ablation of the tissue by applying a first power to the tissue with the electrode, measure a change of temperature of the distal end using the at least one temperature sensor while applying the first power, and estimate a thickness of the tissue in response to the measured change of temperature.

The present disclosure will be more fully understood from the following detailed description of the embodiments thereof, taken together with the drawings, in which:

DETAILED DESCRIPTION OF EMBODIMENTS

Overview

A known procedure for treating atrial fibrillation is radiofrequency ablation of selected portions of the myocardium.

The ablation creates a lesion in the myocardium, and the lesion acts as an electrical impedance to the electropotential wave that travels through the myocardium, so as to correct the wave's incorrect movement.

The amount of ablation, i.e., the energy used in creating the lesion, must be carefully controlled. Under-ablation typically means that the impedance created is insufficient to correct the wave movement; over-ablation can lead to irreversible trauma to the heart. But the amount of ablation required depends on characteristics of the tissue being ablated. These characteristics include different tissue types, which vary through the myocardium, as well as the thickness of the tissue.

While the thickness of the tissue being ablated may be deduced from an image of the heart, such as an MRI (magnetic resonance imaging) image that is typically acquired before the ablation, this data may not be available to the professional performing the ablation. Even if it is available, it may not give the thickness to sufficient accuracy, or the thickness may have changed since acquisition of the image.

Embodiments of the present invention overcome this problem by providing an independent measure of the thickness of tissue being ablated, while the ablation procedure is being performed. The measure relies on the discovery by the inventor that during tissue ablation the temperature measured by the distal end of a probe performing the ablation, for a given irrigation rate and a given power of ablation, varies directly as the thickness of the tissue being ablated. I.e., the thicker the tissue, the higher the temperature measured by the distal end.

Thus, in a typical ablation procedure, a probe distal end is inserted into proximity with the tissue to be ablated, and an initial ablation, typically for a time period between 10 s and 20 s, of the tissue is performed with a first power being applied by the distal end. While the power is being applied, a temperature of the distal end, typically a mean temperature calculated from multiple sensors in the distal end, is measured. The thickness of the tissue being ablated is then estimated from the measured temperature, and a value of the estimated thickness may be displayed to an operator performing the ablation. The estimation typically comprises using a relationship, between the temperature of the distal end, the thickness of the tissue, an injected power to the tissue, and an irrigation rate for irrigating the tissue. The relationship is typically determined prior to performing the initial ablation.

Once the tissue thickness has been estimated, the initial power may be adjusted to reflect the thickness, and the ablation procedure completed with the adjusted power.

DETAILED DESCRIPTION

Figure 1:
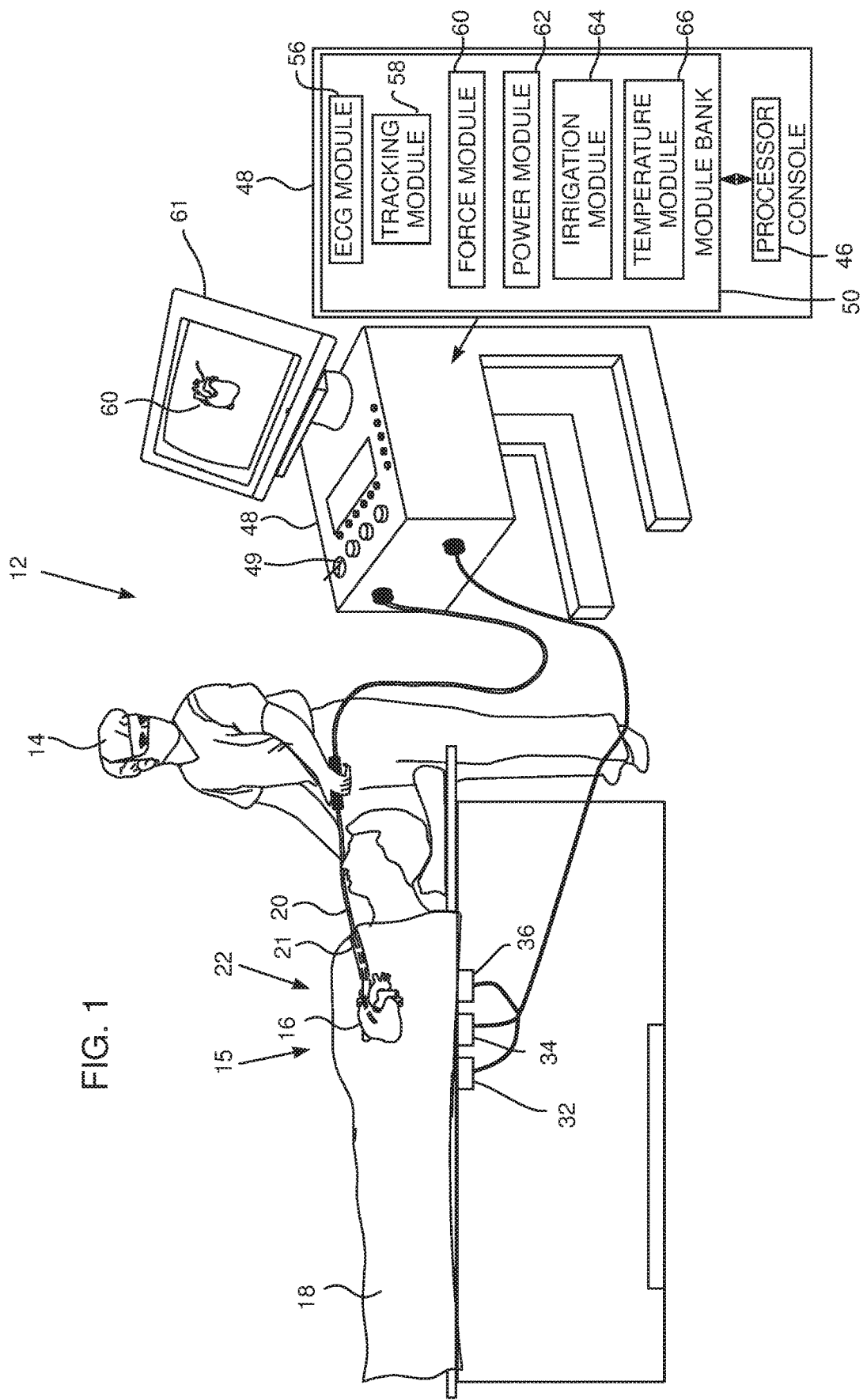
FIG. 1 is a schematic illustration of an invasive medical procedure using apparatus, according to an embodiment of the present invention.
Figure 2:
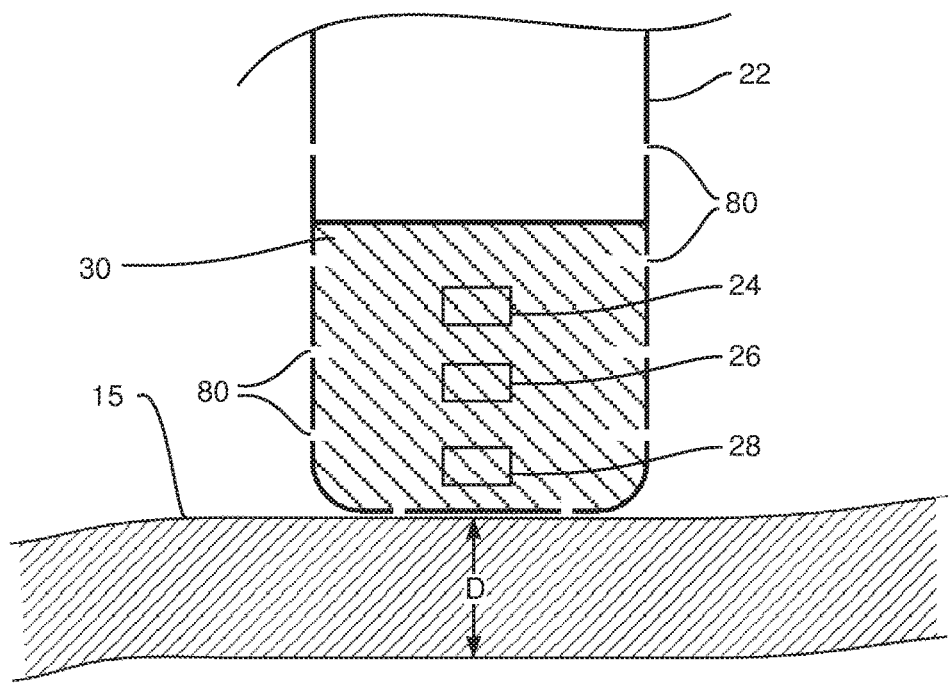
FIG. 2 is a schematic illustration of a distal end of a probe used in the apparatus, according to an embodiment of the present invention.

FIG. 1 is a schematic illustration of an invasive medical procedure using apparatus 12, and FIG. 2 is a schematic illustration of a distal end 22 of a probe 20 used in the apparatus, according to an embodiment of the present invention. The procedure is performed by an operator 14 of apparatus 12. In the following description operator 14 is assumed to be a medical professional, referred to herein as medical professional 14. In the description hereinbelow the procedure is assumed to comprise an ablation of a portion of tissue 15 of a myocardium 16 of the heart of a human patient 18.

In order to perform the investigation, professional 14 inserts probe 20 into a sheath 21 that has been pre-positioned in a lumen of the patient. Sheath 21 is positioned so that distal end 22 of the probe enters the heart of the patient. Distal end 22 comprises a position sensor 24 that enables the location and orientation of the distal end to be tracked, a force sensor 26 that measures the force applied by the distal end when it contacts the myocardium, and one or more temperature sensors 28 that measure the temperature at respective locations of the distal end. Distal end 22 also comprises an electrode 30 which is used to deliver radiofrequency ablation power to myocardium 16 in order to ablate the myocardium. Electrode 30 may also be used to acquire electropotentials from the myocardium, as noted below.

Apparatus 12 is controlled by a system processor 46, which is located in an operating console 48 of the apparatus. Console 48 comprises controls 49 which are used by professional 14 to communicate with the processor. The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 that is displayed on a screen 61.

In order to operate apparatus 12, processor 46 communicates with a module bank 50, which has a number of modules used by the processor to operate the apparatus. Thus, bank 50 comprises an electrocardiograph (ECG) module 56 which acquires and analyzes signals from electrode 30, and a tracking module 58 which receives and analyzes signals from position sensor 24, and which uses the signal analysis to generate a location and an orientation of distal end 22. In some embodiments sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing sensor 24. The radiators are positioned in proximity to myocardium 16, and are configured to radiate alternating magnetic fields into a region in proximity to the myocardium. The Carto® system produced by Biosense Webster, of 33 Technology Drive, Irvine, Calif. 92618, uses such a magnetic tracking system.

Bank 50 also comprises a force module 60, a power module 62, an irrigation module 64, and a temperature module 66. The functions of these modules are explained below.

Force module 60 receives signals from force sensor 26, and from the signals generates a magnitude of the force, herein assumed to be measured in grams, exerted by distal end 22 on tissue 15. In some embodiments the force sensor 26 is configured so that the signals it provides to module 66 enable the module to evaluate a direction of the force exerted by the distal end on tissue 15.

Power module 62 generates the radiofrequency power that is conveyed to electrode 30, and that is applied by the electrode to ablate tissue 15. Processor 46 and module 62 are able to adjust a power level P, herein assumed to be measured in Watts, delivered by the electrode, as described in more detail below.

Irrigation module 64 controls a rate of flow V, herein assumed to be measured in mL/min, of irrigation fluid, typically normal saline solution, supplied to distal end 22. The irrigation fluid is expelled from irrigation holes 80 in the distal end.

Temperature module 66 receives signals from one or more temperature sensors 28, and determines the temperatures registered by each of the sensors. Typically, in the case of multiple sensors 28 the module determines a mean temperature T of distal end 22. Additionally, in the case of multiple sensors, the module may produce a map of the temperature distribution of the distal end.

The inventor has found that during an ablation procedure an overall thickness D of tissue 15 being ablated affects the mean change of temperature ΔT measured by one or more sensors 28. In particular, for a given power P applied over a given time, and for a given irrigation rate V of fluid through the distal end, the change of temperature ΔT is large for large values of D and is small for small values of D. This relationship holds for an initial non-steady state of ablation, as well as for a steady ablation state. The inventor believes that this relationship between the change of temperature ΔT and the overall thickness D is due to the heat energy retained by the tissue. I.e., tissue having a large D retains more heat energy than tissue having a small D.

The relationship may be quantified, to a first approximation, by the following equation:

$$D = K_1 \cdot \Delta T \quad (1)$$

where D and ΔT are as defined above, and where $K_1$ is a constant depending, inter alia, on the values of P (power) and V (irrigation rate).

Since distal end 22 has a substantially constant heat capacity, the actual value of ΔT increases as the power P increases and decreases as the irrigation rate V increases.

In addition, the relationship of equation (1) also depends on the force F applied by the distal end, so that a more general expression for D is given by equation (2):

$$D = f(V, P, CF, \Delta T) \quad (2)$$

where f is a function, and where
V is the irrigation rate,
P is the power applied,
CF is a contact force applied by the distal end, and
ΔT is the temperature increase of the distal end.

In one embodiment equation (2) can be rewritten as equation (3):

$$D = K_2 \cdot \frac{V}{P \cdot CF} \cdot \Delta T \quad (3)$$

where $K_2$ is a constant, and where D, ΔT, V, CF and P are as defined above.

It will be understood that in equations (1) and (3) constants $K_1$ and $K_2$ have dimensions, and that since they are dependent on the heat capacity of distal end 22, their values depend on the type of distal end being used.

Consideration of equations (1) and (3) illustrates that D varies as ΔT when processor 46 uses values of P, CF, and V that have been normalized.

In embodiments of the present invention, professional 14 may determine a value for $K_1$ and/or $K_2$, corresponding to quantifying the relationships referred to above, by ablation of tissue for a given time, using measured values of D, ΔT, P, CF, and V. Alternatively or additionally, professional 14 may quantify the relationships by storing the measured values of D, ΔT, P, CF, and V in a look-up table, and using extrapolation and/or interpolation to derive values of D, ΔT, P, CF, and V not in the look-up table. Typically, quantifying the relationships as described above, by determining the value of $K_1$ and/or $K_2$ and/or storing values of D, ΔT, P, CF, and V in a look-up table, is implemented prior to performing the procedure referred to above.

Figure 3:
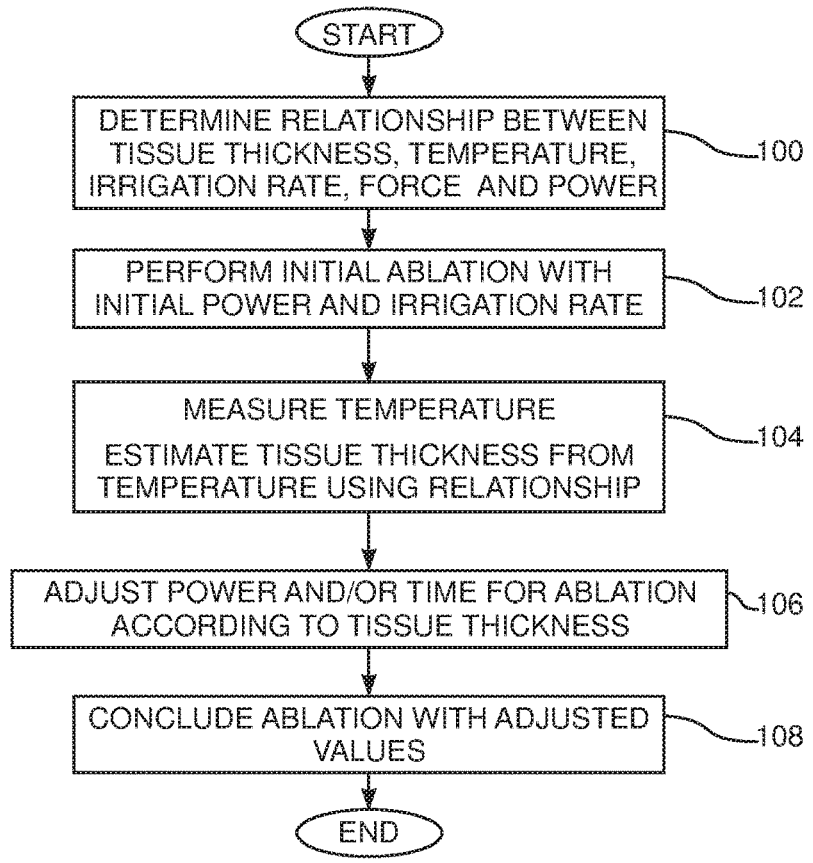
FIG. 3 is a flowchart of steps followed by a professional in performing the procedure, according to an embodiment of the present invention.

FIG. 3 is a flowchart of steps followed by professional 14 in performing the procedure, according to an embodiment of the present invention. In a preparatory step 100, the relationship between D, ΔT, P, CF, and V is determined. The relationship may be as described above, e.g., as equation (1) by evaluating $K_1$, or as equation (3) by evaluating $K_2$, or as a look-up table. A probe having a distal end similar to distal end 22 is used to perform the evaluations and/or generate the look-up table. For simplicity in the following description the relationship is assumed to be equation (1), and those having ordinary skill in the art will be able to adapt the description in the case equation (2) or equation (3) or a look-up table is used.

In an initial ablation step 102, professional 14 inserts distal end 22 so that electrode 30 contacts a selected portion of tissue 15 of myocardium 16, and force module 60 and processor 46 record a contact force CF sensed by force sensor 26. Once in contact with tissue 15, the professional sets a flow rate V of irrigation to the distal end, and also selects an initial value of the power P to be applied to the tissue. Typically, the value for V is set within a range 10-20 mL/min, and the value of P is set at 20-30 W, but both V and P may have values outside these ranges.

In some embodiments professional 14 may select P based on a targeted ablation index value for the lesion to be formed in tissue 15. As is known in the art, an ablation index is a function, having a value that changes as ablation proceeds, which provides an estimate of the size of a lesion produced by the ablation of a tissue of known type. The estimate provided by the index depends on the values of the contact force CF and power P measured during the ablation, as well as on the period of time of the ablation. Ablation indices are described in an article entitled "Ablation Index-guided Pulmonary Vein Isolation for Atrial Fibrillation may Improve Clinical Outcomes in Comparison to Contact Force-guided Ablation" to Hussein et al., presented at the 2016 Heart Rhythm Congress, and in U.S. Patent Application 2017/0014181 to Bar-Tal et al. Both documents are incorporated herein by reference.

Equation (4) below gives an expression for an ablation index:

$$D_{est} = (C \int_0^t CF^\alpha(\tau) P^\beta(\tau) d\tau)^\delta = \text{Ablation Index} \quad (4)$$

where C is a constant having a value depending on the type of tissue being ablated; in one embodiment C has an approximate value of 0.002, α is an exponent having a value typically in the range 0.6-0.8, β, is an exponent having a value typically in the range 1.4-1.8, δ is an exponent having an approximate value of 0.35, $D_{est}$ is an estimate of the depth of a lesion achieved by ablating for a time t, with instantaneous constant force CF(τ) and instantaneous power P(τ), and where τ represents a time variable.

If the contact force and the power are assumed to be constant, having respective values $\overline{CF}$ and $\overline{P}$ during an ablation procedure that is to take a time t, then equation (4) may be rewritten as equation (5):

$$D_{est} = (C \, \overline{CF}^\alpha \overline{P}^\beta t)^\delta \quad (5)$$

The right side of equation (5) is an ablation index that professional 14 may use to set an initial value of power P, by solving the equation for $\overline{P}$ using the measured value of force CF, an assumed value for the time t of ablation, an estimate $D_{est}$ of the thickness of tissue 15, and an estimate of C. The professional may estimate $D_{est}$ on the basis of a previously acquired image of tissue 15, such as from an MRI scan, or from knowledge of the location of tissue 15. The professional may estimate C based on the type of tissue being ablated.

For clarity and simplicity, in initial ablation step 102 the professional is assumed to use the ablation index of equation (5) to estimate an initial power P to be used. In addition, in the remaining description of the flowchart, except where otherwise stated, processor 46 is assumed to use the ablation index of equation (5) to provide to the professional an estimate $D_{est}$ of the depth of ablation achieved while ablation is being performed. Those having ordinary skill in the art will be able to adapt the description, mutatis mutandis, for a case of a different ablation index.

Initial ablation step 102 is initially performed for a relatively short time, typically of approximately 10 s-20 s. At the conclusion of step 102 the processor stores the value of $D_{est}$, the estimated depth of the lesion formed in the initial ablation. The flowchart then proceeds to a tissue thickness estimation step 104, wherein the processor estimates a thickness of tissue 15.

In step 104, the processor determines a value of ΔT, using one or more temperature sensors 28. The processor then uses the relationship found in preparatory step 100, e.g., equation (1), to evaluate the overall tissue thickness D of tissue 15.

At this stage the processor has an evaluation $D_{est}$ of the depth of the lesion, as found at the conclusion of step 102, and an estimate D of the overall thickness of tissue 15. Typically, values of $D_{est}$ and D are presented to professional 14 on screen 61.

In an adjustment step 106, the processor compares the values of $D_{est}$, the estimated depth of the lesion, and D, the overall thickness of tissue 15. The difference $(D-D_{est})$ provides the processor with a numerical estimate of how much tissue is left to be ablated so that tissue 15 is completely ablated.

Using the value of $(D-D_{est})$ the professional may use the processor to adjust, or leave unadjusted, values of factors in the ablation index, such as the time t of ablation and/or the power P applied, in order to achieve complete ablation of tissue 15.

In a concluding step 108, the professional applies the values of factors of the ablation index determined in step 108 until tissue 15 has been completely ablated.

The description above of steps of the flowchart assumes that professional 14 uses an ablation index in determining values of power to be applied during an ablation procedure. The ablation index acts as an aid to the professional in deciding values of parameters, such as power and time period of ablation, to be used during an ablation procedure. However, it will be understood that the professional may not use an ablation index in deciding values of such parameters, while still using the description of tissue thickness estimation step 104 to estimate the thickness of tissue being ablated, and may adapt the flowchart description, mutatis mutandis, for such a case. It will this be understood that the scope of the present invention includes cases where an ablation index is not used.

It will furthermore be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
performing an initial ablation of a tissue from a start to an end of a first time period using an electrode in a probe distal end to apply a first power to a proximal surface of the tissue;
measuring a change of temperature of the distal end from the start to the end of the first time period;
estimating an overall thickness of the tissue in response to the measured change of temperature, the overall thickness being a measure of a distance between the proximal surface of the tissue and a distal surface of the tissue;
in response to the estimated overall tissue thickness, computing at least one of a second power required and a second time period for ablation, to complete ablation of the tissue; and
performing a subsequent ablation of the tissue using the computed at least one of the second power and the second time period for ablation.

2. The method according to claim 1, further comprising determining a relationship between the change of temperature of the distal end and the overall thickness of the tissue, and using the relationship in estimating the overall thickness of the tissue.

3. The method according to claim 2, wherein the relationship includes a force applied by the probe distal end during the initial ablation.

4. The method according to claim 1, further comprising determining an estimated lesion depth after performing the initial ablation.

5. The method according to claim 2, wherein the relationship includes the first power applied to the tissue and an irrigation rate for irrigating the tissue during the initial ablation.

6. The method according to claim 1, further comprising selecting the first power so that the initial ablation ablates the tissue to a predetermined estimated lesion depth.

7. The method according to claim 4, further comprising computing the at least one of the second power required and the second time period in response to a difference between the estimated overall thickness of the tissue and the determined estimated lesion depth.

8. The method according to claim 1, further comprising using an ablation index of estimated lesion depth to determine at least one of the first power and the second power.

9. A method, comprising:
performing an ablation of a tissue using an electrode in a probe distal end to apply a power to a proximal surface of the tissue;
measuring a change of temperature of the distal end while applying the power during the ablation; and
estimating an overall thickness of the tissue in response to the change of temperature measured during the ablation, the overall thickness being a measure of a distance between the proximal surface of the tissue and a distal surface of the tissue.

10. The method according to claim 9, further comprising displaying a value of the estimated overall thickness of the tissue to an operator performing the ablation.

11. An apparatus, comprising:
a probe having a distal end;
an electrode located on the distal end configured for contact with tissue during ablation;
at least one temperature sensor in the distal end; and
a processor, configured to:

perform an initial ablation of the tissue from a start to an end of a first time period by applying a first power to a proximal surface of the tissue with the electrode, measure a change of temperature of the distal end using the at least one temperature sensor from the start to the end of the first time period, estimate an overall thickness of the tissue in response to the measured change of temperature, the overall thickness being a measure of a distance between the proximal surface of the tissue and a distal surface of the tissue, in response to the estimated overall thickness, compute at least one of a second power required and a second time period for ablation, to complete ablation of the tissue, and perform a subsequent ablation of the tissue using the computed at least one of the second power and the second time period for ablation.

12. The apparatus according to claim 11, wherein the processor is configured to determine a relationship between the change of temperature of the distal end and the overall thickness of the tissue and use the relationship in estimating the overall thickness of the tissue.

13. The apparatus according to claim 12, wherein the relationship includes a force applied by the probe distal end during the initial ablation.

14. The apparatus according to claim 12, wherein the processor is configured to determine an estimated lesion depth after performing the initial ablation.

15. The apparatus according to claim 12, wherein the relationship includes the first power applied to the tissue and an irrigation rate for irrigating the tissue during the initial ablation.

16. The apparatus according to claim 11, wherein the processor is configured to select the first power so that the initial ablation ablates the tissue to a predetermined estimated lesion depth.

17. The apparatus according to claim 14, and wherein the processor is configured to compute the at least one of the second power required and the second time period in response to a difference between the estimated overall thickness of the tissue and the determined estimated lesion depth.

18. The apparatus according to claim 11, wherein the processor is configured to use an ablation index of estimated lesion depth to determine at least one of the first power and the second power.

19. An apparatus, comprising:
a probe having a distal end;
an electrode located on the distal end configured for contact with tissue during ablation;
at least one temperature sensor in the distal end; and
a processor, configured to:
perform an ablation of the tissue by applying a power to a proximal surface of the tissue with the electrode,
measure a change of temperature of the distal end using the at least one temperature sensor while applying the power during the ablation, and
estimate an overall thickness of the tissue in response to the change of temperature measured during the ablation, the overall thickness being a measure of a distance between the proximal surface of the tissue and a distal surface of the tissue.

20. The apparatus according to claim 19, and comprising a screen configured to display a value of the estimated overall thickness of the tissue to an operator performing the ablation.

* * * * *